United States Patent
Fadler

(10) Patent No.: US 7,418,080 B2
(45) Date of Patent: Aug. 26, 2008

(54) SUPPORT AND RADIATION THERAPY SYSTEM

(75) Inventor: Franz Fadler, Hetzles (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/542,304

(22) Filed: Oct. 2, 2006

(65) Prior Publication Data

US 2007/0081632 A1 Apr. 12, 2007

(30) Foreign Application Priority Data

Oct. 10, 2005 (DE) .................... 10 2005 048 391

(51) Int. Cl.
- *A61N 5/10* (2006.01)
- *H05G 1/64* (2006.01)
- *H01J 31/50* (2006.01)

(52) U.S. Cl. .................... 378/65; 378/98.8; 378/189

(58) Field of Classification Search ............. 378/20, 378/37, 65, 167, 177, 189, 195, 208
See application file for complete search history.

(56) References Cited

U.S. PATENT DOCUMENTS

| | | | |
|---|---|---|---|
| 5,538,214 A | 7/1996 | Sinila | |
| 6,242,742 B1 | 6/2001 | Geay et al. | |
| 6,325,537 B1 | 12/2001 | Watanabe | |
| 6,630,676 B2 * | 10/2003 | Takemoto | 250/370.09 |
| 6,715,981 B1 * | 4/2004 | Harsch et al. | 414/752.1 |
| 6,888,919 B2 | 5/2005 | Graf | |
| 6,979,123 B2 | 12/2005 | Barta et al. | |
| 7,065,176 B2 * | 6/2006 | Moermond et al. | 378/58 |
| 7,265,356 B2 * | 9/2007 | Pelizzari et al. | 250/370.09 |
| 2002/0080921 A1 * | 6/2002 | Smith et al. | 378/189 |
| 2004/0076263 A1 * | 4/2004 | De Godzinsky et al. | 378/197 |
| 2004/0120452 A1 | 6/2004 | Shapiro et al. | |

FOREIGN PATENT DOCUMENTS

| | | |
|---|---|---|
| DE | AT 156705 | 8/1939 |
| DE | 4402347 | 8/1995 |
| EP | 1 099 411 A2 | 5/2001 |
| EP | 1468651 | 10/2004 |
| FR | 2878016 A1 | 5/2006 |
| JP | 2001218133 A | 8/2001 |

OTHER PUBLICATIONS

International Search Report dated Feb. 20, 2007 for GB0619712.3.
German Office Action dated Jun. 13, 2006 (English translation enclosed).

* cited by examiner

*Primary Examiner*—Irakli Kiknadze
(74) *Attorney, Agent, or Firm*—Brinks, Hofer, Gilson & Lione

(57) ABSTRACT

A support and radiation therapy system is provided. The support includes an elongated support arm that is longitudinally adjustable. A first arm is rotatable in the support arm about a first axis that is perpendicular to the support arm. A flat detector is rotatable in the first arm about a second axis that is parallel to the first axis. The detector is essentially parallel to the support arm. A motor is operative to drive the rotation of the first arm. A first gear is operative to rotate the first arm and is connected to the motor. A second gear is operative to rotate the detector and is connected to the motor. The second gear is operative to rotate contrary to the first gear.

19 Claims, 4 Drawing Sheets

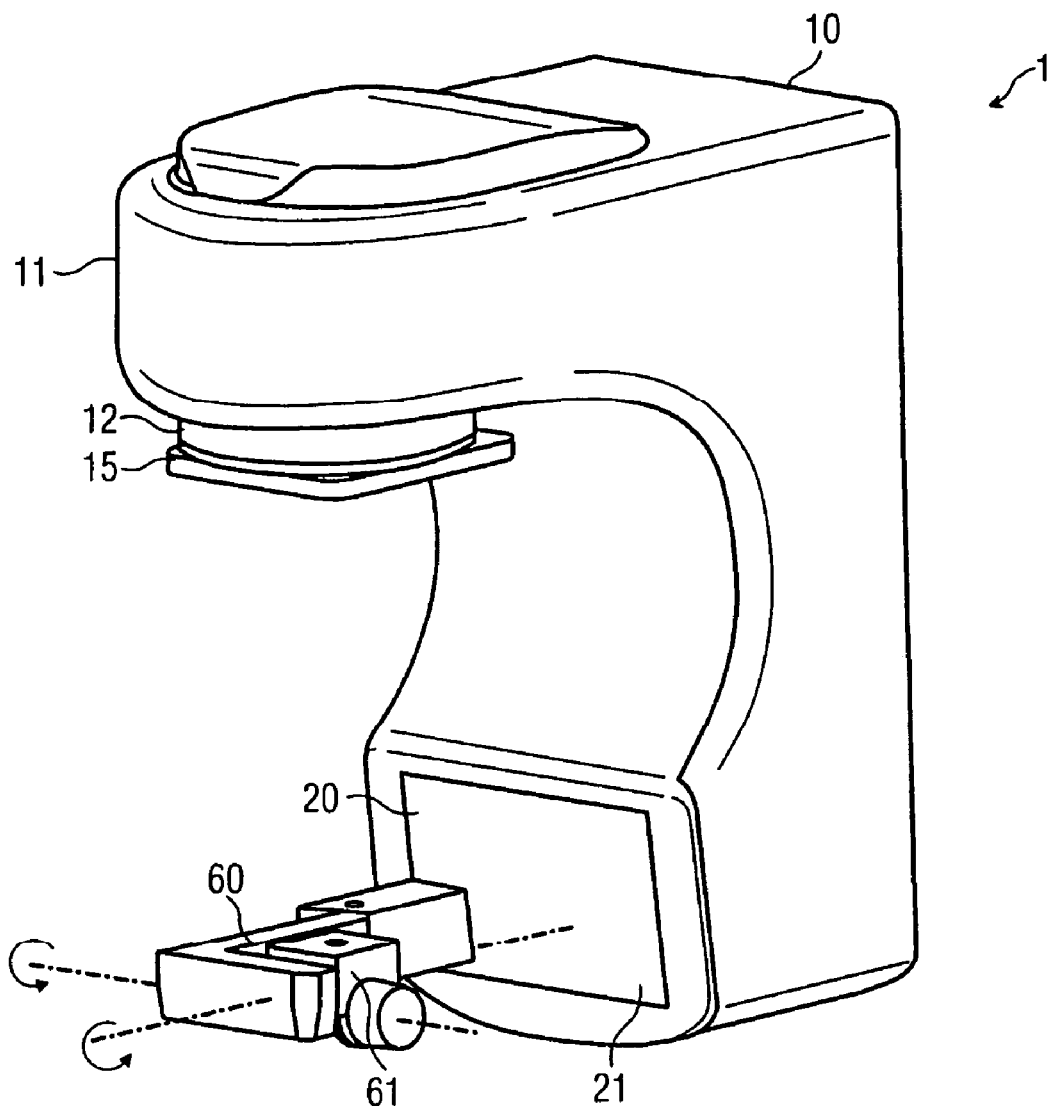

SUPPORT AND RADIATION THERAPY SYSTEM

The present patent document claims the benefit of the filing date of DE 10 2005 048 391.7, filed Oct. 10, 2005.

BACKGROUND

1. Field

The present embodiments relate to a support for a radiation therapy system.

2. Related Art

Radiation systems are used in medical therapy for irradiating diseased tissue, for example, tumor tissue. Suitable radiation types of therapy include, for example, high-energy X-radiation in the megavolt range; lightweight particle radiation (i.e. electrons or positrons or protons); and heavy particle radiation (i.e. oxygen or carbon ions). Because of the radiation, the bonds of the living tissue are destroyed or atoms are ionized. These alterations can cause destruction or death of the tissue. Although this effect is intended with regard to the tumor tissue or diseased tissue, this effect must be avoided in healthy tissue. In a desired radiation system, the radiation dose administered to diseased tissue should be increased and the radiation dose administered to the healthy tissue should be reduced.

Generally, the placement of the radiation dose with regard to the penetration depth into the irradiated tissue is achieved by a suitable choice of both the type and the energy of the radiation. The two-dimensional, lateral localization of the radiation in terms of the radiation direction is achieved by the circumference of the beam and by its contour. Sharp focusing allows coarse localization by diaphragms, and contoured localization by collimators, for example, multi-leaf collimators, which allow many different contours. When irradiating an organ, for example, it is possible to shape the beam of rays so that the beam corresponds substantially to the contour of the organ. Accordingly, only a minimum amount of tissue located around the organ is irradiated.

The contour of the beam is monitored both continuously and in each individual case. The monitoring increases the operating safety and avoids risk of the patient being exposed to unnecessarily high radiation exposure caused by radiation not accurately aimed at the desired organ. To help control the monitoring, visible light can, for example, pass through the beam shaping device, or in other words the focusing, diaphragms and collimators. The visible light makes optical control possible. The radiation type must have the same optical properties as visible light. Detector elements, for example, X-ray image detectors, are used at the position where a patient is to be irradiated. For example, in the case of X-radiation, a control image of the beam is obtained from the detector element.

To properly prepare for the irradiation, both an exact establishment of the contour of the beam and an equally exact positioning of the patient to be irradiated are necessary. The three-dimensional position of the patient's tissue to be irradiated is determined with the greatest possible accuracy. This three-dimensional position is placed as precisely as possible in the active center or isocenter of the radiation system. Only the exact positioning at the isocenter assures that the contour of the beam is precisely congruent with the contour of the tissue to be irradiated. The position of the tissue to be treated is determined by a diagnostic system, which need not be identical with the therapy system. The positioning of the tissue, which takes place after determining the three-dimensional position, involves major possibilities of error, which can be a hindrance to exact positioning.

To avoid the possibility of error, a diagnostic and therapy system are combined. In this combined system, a patient is first diagnosed and then treated in the same position. Inaccuracies from an intervening repositioning of the patient and from an intervening positioning of the therapy system are avoided. The three-dimensional orientation of the therapy component of the system to the diagnostic component is fixed and increases the positioning accuracy of the equipment.

When disposing the therapy component relative to the diagnostic component, a distinction is made between two possible configurations. First, the beam path of the diagnostic system can differ three-dimensionally from the beam of the therapy system. For example, the diagnostic radiation extends perpendicular to the therapeutic radiation. For example, if the patient is treated with a vertical beam path, then the diagnostic beam path is horizontal. The different three-dimensional course does involve inaccuracies, because only different three-dimensional coordinates are able to be determined. In this example, the horizontal diagnostic radiation is suitable for determining the vertical three-dimensional coordinate of the tissue. The horizontal three-dimensional coordinates are determined by the contouring of the therapeutic beam of rays. Alternatively, the various equipment components are spaced apart from one another three-dimensionally without interfering with one another.

U.S. Pat. No. 6,888,919 discloses a radiotherapy system, which has therapy components disposed in a first gantry. The diagnostic components are disposed in a second gantry. The gantries are movable independently of one another and allow various beam path configurations to be established. Each gantry requires its own free space for motion and includes mechanical components that are located around the patient in the immediate vicinity of the therapy area.

Second, a constellation is selected in which the axis of the diagnostic beam path coincides three-dimensionally with that of the therapeutic beam path. The diagnosis and therapy have the same optical geometry, which increases the accuracy. The various equipment components are disposed in the same beam path and may interfere with one another. The space available for installation is reduced and the components are integrated into the diagnostic and/or therapy system. The components are adapted to one another in a space-saving way.

In an example, an X-radiation therapy system, a high-energy X-radiation source, a less high-energy further X-radiation source, and at least one X-ray image detector in the less high-energy region are disposed in the same beam path. In addition, an X-radiation detector in the high-energy area is used. Both the patient and the therapist should have as much space available as possible, so as not to excessively limit the treatment options and patient comfort.

Austrian Patent Disclosure AT 156705 B discloses a device for X-ray production of images of slices or layers of the body, or of both slices and layers of the body. The X-ray tube and the holder for the image-collecting layer (cassette holder) are pivotable about an axis located in the plane of the body section to be imaged. The X-ray tube and holder are pivotable by the disposition of a double lever on both arms. The X-ray that passes through any point of the body section to be imaged always strikes the same point of the image layer, which is kept parallel to the section plane in the pivoting motion.

SUMMARY

In one embodiment, a support includes an elongated support arm that is longitudinally adjustable. A first arm is rotatable in the support arm about a first axis perpendicular to the support arm. A flat detector element is rotatable in the first arm about a second axis that is parallel to the first axis. The detector element is essentially parallel to the support arm. The detector element is operative to remain parallel to the support arm during the rotation of the first arm. A motor is operative to drive the rotation of the first arm. A first gear is operative to rotate the first arm and is connected to the motor. A second gear is operative to rotate the detector element and is connected to the motor. The second gear is operative to rotate contrary to the first gear.

The kinematics of the arm and detector element with a motor and two contrary-operation gears provides a space-saving, flexible construction and precise guidance of the detector element. In this embodiment, only two rotary bearings are needed. The two rotary bearings are embodied with high precision.

In comparison, a conventional parallelogram kinematic embodiment, for example, is based on at least four rotary bearings, which would each have to be adapted to one another and in addition adapted to the parallelogram struts. The struts of the conventional parallelogram have to be adapted to one another as well. The many mutual dependencies of the conventional parallelogram reduce the precision in guiding the motion of the detector element and increase the production cost disproportionately. Depending on the dimensioning of the conventional parallelogram construction, the space required for the construction increases, in comparison to the single-strut arm. The radiation systems typically allow the rotation of the therapeutic and diagnostic rays about the isocenter, and as a result, the orientation of the arm and detector element is rotated as well. With the attendant change in the direction of gravity, increased demands in terms of precision of the guidance of motion are additionally made, which increases the effort and expense for construction and production. This expense is kept to a minimum by providing that only a small number of construction elements be provided for the kinematics.

In one embodiment, the motor is connected to the first gear by a shaft and to the second gear by a belt or chain. The shaft precisely guides the motion of the first gear. The belt or chain drive of the second gear is accurate and requires minimal structural effort and expense.

In another embodiment, a radiation device includes a support that has one support arm with precisely one telescoping rail and precisely one telescoping arm. Precisely one single-strut arm is mounted in the support arm. Precisely one lateral drive mechanism is mounted in the arm. Precisely one detector element is mounted by the lateral drive mechanism.

BRIEF DESCRIPTION OF THE DRAWINGS

FIG. 4 shows the radiation device with a low-energy X-radiation source.

DETAILED DESCRIPTION

Figure 1:
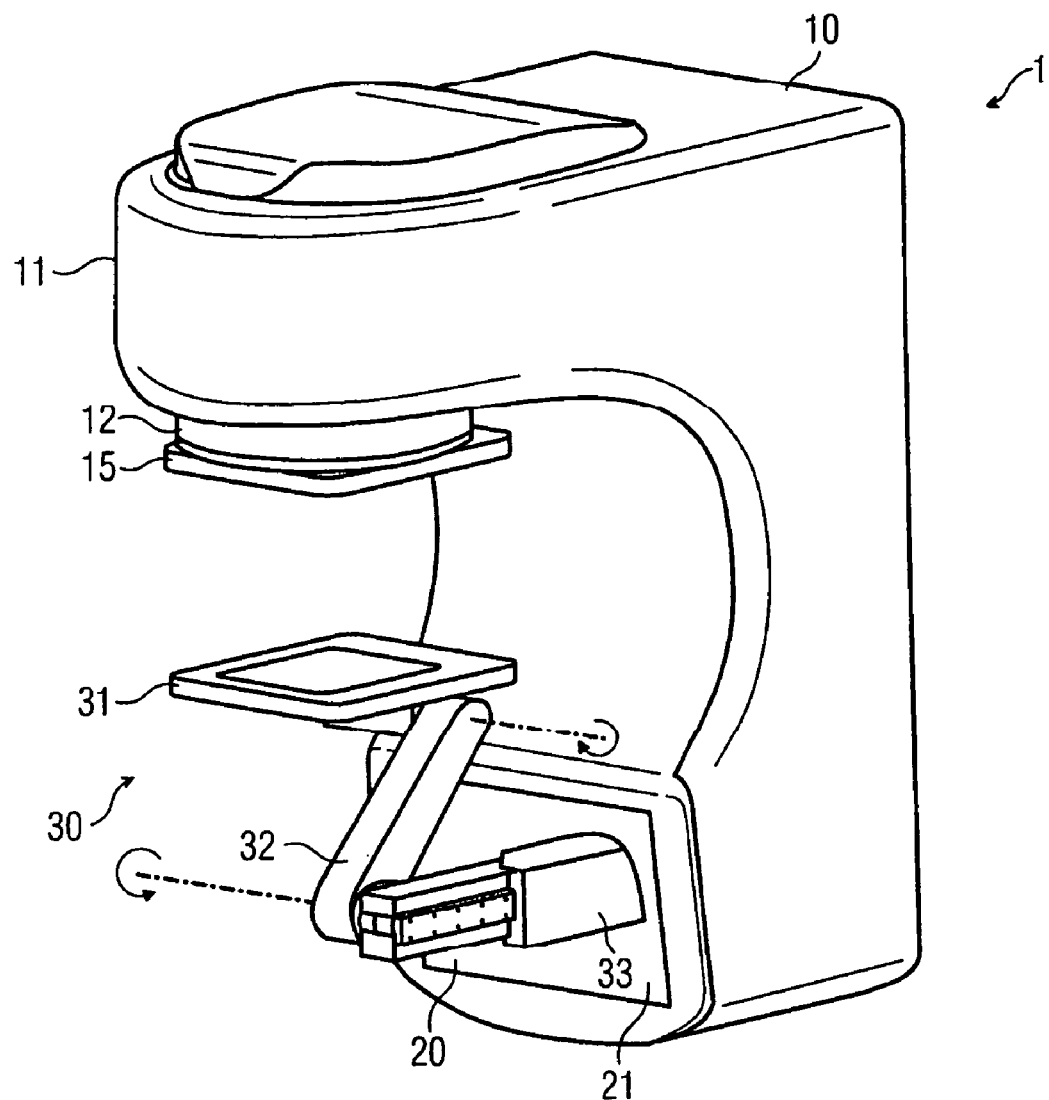
FIG. 1 shows a radiation device with a support and a detector element.

In one embodiment, as shown in FIG. 1, a radiation device 1 includes a gantry 10. The gantry 10 is supported rotatably about a horizontal axis and supports the essential functional components of the radiation device 1.

The gantry 10 has an emitter head 11, from which the therapeutic radiation is emitted, for example, in the direction of the MV detector 31 (downward in FIG. 1). A patient (not shown) to be irradiated is positioned on a patient positioning device (also not shown), with the body part that is to be irradiated located under the emitter head 11. A beam shaper 12 is provided on the emitter head 11. The beam shaper 12 shapes the contour of an irradiated beam. In alternate embodiments, the beam shaper 12 includes, for example, a focusing device, one or more diaphragms, and/or one or more collimators.

A kV detector 15 is disposed below the beam shaper 12. The kV detector 15 detects the X-radiation in the kV energy range. The kV detector 15 makes it possible to detect the contour of an X-ray beam passing through and an X-ray dose passing through. For example, if irradiation of a patient is done with dosage measurement in the kV detector 15 and further dosage measurement after passage through the patient, then a value for the dosimetry can be obtained from the difference between the two dosage measurements.

In one embodiment, a tripod or support 30 is mounted on the gantry. The support 30 is on the side of the gantry 10 diametrically opposite the emitter head 11. The support 30 includes a telescoping rail 33 that extends through a blind 21. The telescoping rail 33 is a component of a support arm in which an arm 32 is supported rotatably about a first axis. The first axis extends perpendicular to the longitudinal direction of the support arm (the horizontal direction in the drawing). Alternatively, the first axis may also be oriented in a direction other than horizontally depending on the rotary position of the gantry 10.

The arm 32 is embodied with a single strut. For example, the single strut allows a compact, simple construction.

In one embodiment, an MV detector 31 is supported by the arm 32 rotatably about a second axis. The second axis extends parallel to the first axis. The MV detector 31 is embodied two-dimensionally and extends substantially in a plane that is oriented parallel to the longitudinal extent of the support arm and also parallel to the first and second axes of rotation. In one embodiment, the detector plane is perpendicular to the central beam path of a treatment beam emerging from the emitter head 11. For example, rotation of the arm 32 causes the MV detector 31 to be raised or lowered relative to the support arm. In one embodiment, the telescoping mechanism of the support arm is simultaneously moved inward or outward to compensate for a simultaneous longitudinal displacement. As shown in FIG. 1, the support 30 and the MV detector 31 form approximately the shape of a Z. During operation, the motion control maintains the Z shape of the MV detector 31 upon rotation of the arm 32. Accordingly, the combination of the MV detector 31, arm 32, and telescoping arm 33 will therefore hereinafter also be called the Z drive.

In one embodiment, the MV detector 31 detects an image of the contour of a high-energy therapeutic X-ray beam that is in the MV range. For example, a desired contour of the therapeutic radiation can be monitored. The MV detector 31 is located below a patient who is to be irradiated and is capable, in collaboration with the kV detector 15, of detecting dosage measurement values for use in the dosimetry.

Figure 2:
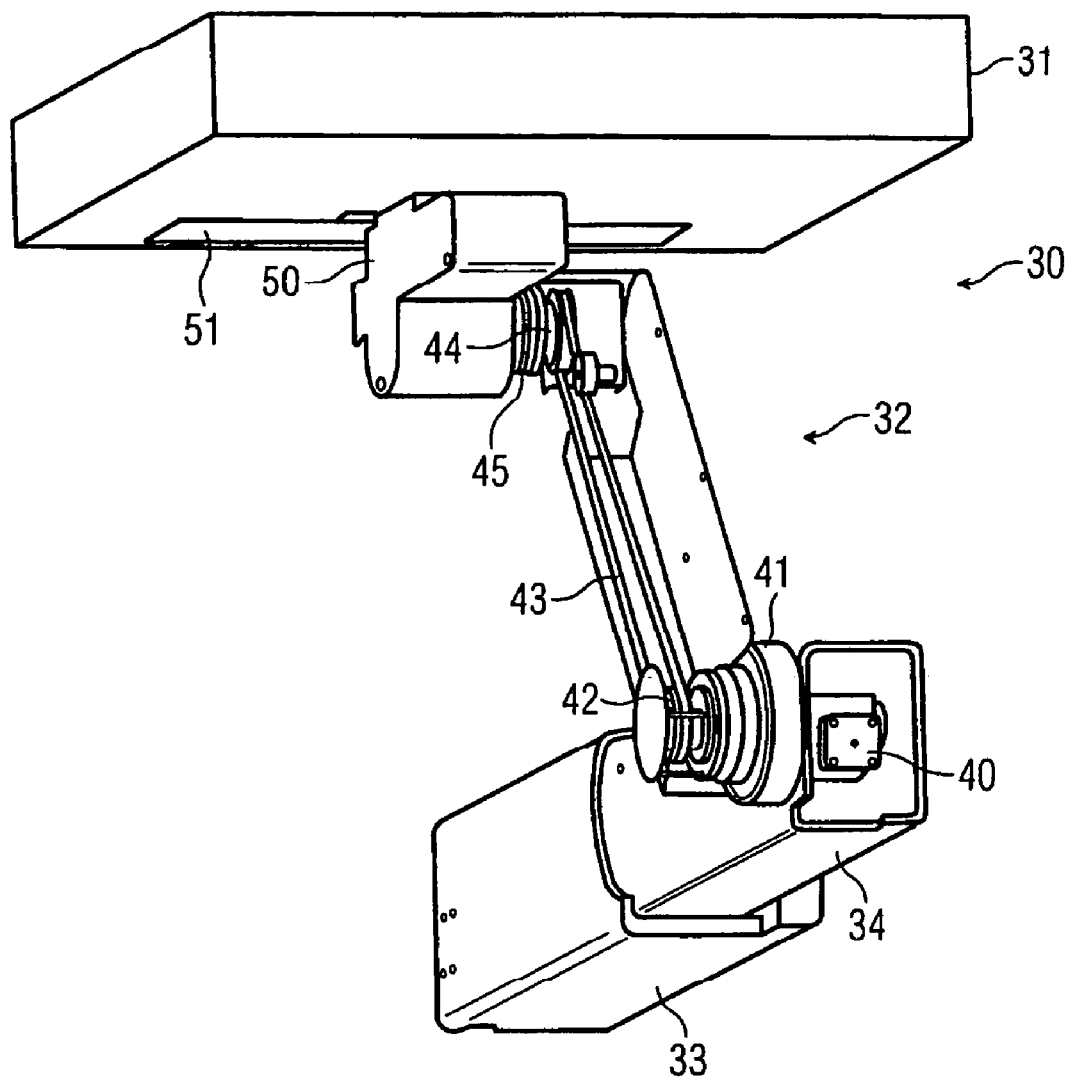
FIG. 2 shows the support and detector element in a front elevation view.

FIG. 2 illustrates the support 30 and the MV detector 31 from a front elevation view. Blinds of the support that are not essential to the function have been left out for the sake of better explanation. Otherwise, the same reference numerals as in FIG. 1 are used.

In one embodiment, the telescoping arm 34 is guided in the telescoping rail 33. In FIG. 2, the front of the telescoping rail 33 is open so that the motor 40 mounted in the telescoping arm 34 can be seen. However, the end of the telescoping rail can be closed. The motor 40 is connected via a shaft (not identified by reference numeral) with a gear 41, which in turn is connected to the arm 32. The motor 40 drives a rotation of the arm 32 via the gear 41. A pulley 42 is connected to the shaft. The pulley 42 is driven jointly upon rotation of the arm 32. A belt 43 is driven by the pulley 42. The belt 43 drives a further pulley 44.

A further gear 45 is connected to the further pulley 44 and is jointly driven upon rotation of the arm 32. The gear 45 runs contrary to the further gear 41 and rotates a lateral drive mechanism 50. The gears 41 and 45 run contrary at exactly the same rotary speed. The lateral drive mechanism 50 is rotated at exactly the same speed as, but contrary to, the arm 32. The MV detector 31 is supported in the lateral drive mechanism 50. For example, the parallel orientation of the MV detector 31 is maintained upon rotation of the arm 32.

In one embodiment, the MV detector 31 is supported in the lateral drive mechanism by a rail 51 to increase the variability. The MV detector 31 is displaceable perpendicular to the longitudinal direction of the telescoping rail 33 and telescoping arm 34. For example, this kind of displacement does not substantially affect the parallel orientation.

In one embodiment, the motor 40, the pulleys 42, 44, and the belt 43 and other details are concealed by blinds and/or coverings, in the completely installed state of the support.

Figure 3:
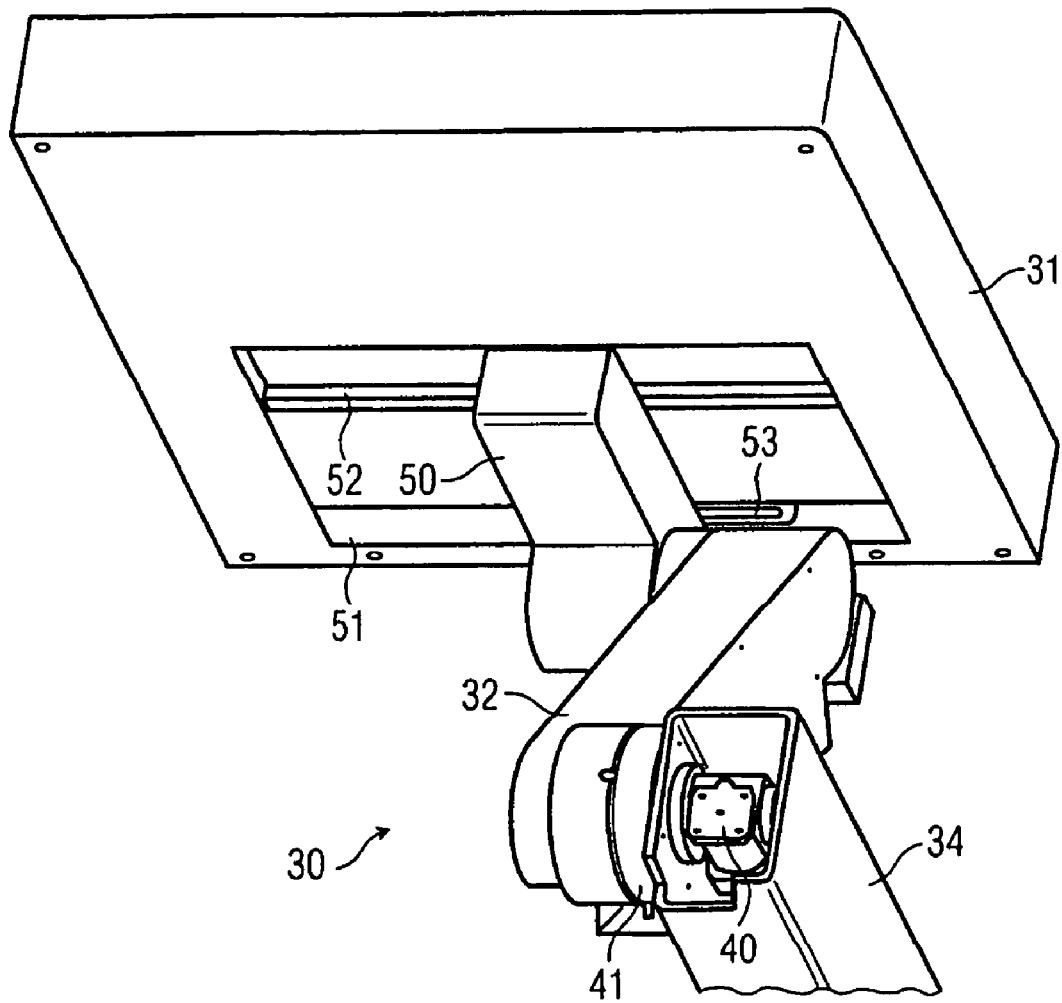
FIG. 3 shows the support and detector element seen from below.

FIG. 3 schematically illustrates the support 30 and the MV detector 31 from below in perspective. The same reference numerals are used as in the above FIG. 2. As shown in FIG. 3, the coverings and blinds of the arm 32 are installed so that its interior features are therefore not visible. Only the front covering of the telescoping arm 34 is not in place, and the motor 40 is still visible. The gear 41 cooperates in collaboration with the motor 40 and the further gear (not shown in FIG. 3) on the upper end of the arm 32. FIG. 3 shows the components of the lateral drive mechanism 50.

In one embodiment, as shown in FIG. 3, the MV detector 31 has two parallel, transversely extending rails 51 and 52. The MV detector 31 is supported transversely displaceably on the lateral drive mechanism 50. The lateral drive mechanism 50 has a motor (not shown), which drives a transverse or lateral motion of the MV detector 31. The motor drives a chain 53, which is connected to the carriage of the MV detector 31.

FIG. 4 schematically illustrates a radiation device 1 with a different equipment constellation in perspective. In one embodiment, the radiation device 1 includes a gantry 10 that supports an emitter head 11 with a beam shaper 12. Positioned below the emitter head 11 is a beam shaper 12. Below the beam shaper 12 is a kV detector 15, which assists in producing a diagnostic image of a patient (not shown). For example, when generating the diagnostic X-radiation, a kV X-radiation emitter 61 is located on the opposite end of the gantry 10 (below the emitter head 11).

In one embodiment, the support 30 and the MV detector 31 are returned to the parking position behind the blind 21. The kV X-ray emitter 61 is mounted in the immediate vicinity of the blind 21, behind the blind 20 in the gantry 10. The kV X-ray emitter 61 is supported by a telescoping mechanism 60, which is, for example, essentially identical to that of the support 30. The kV X-ray emitter 61 is supported rotatably about two axes in the telescoping mechanism 60. In another embodiment, for example, an X-ray beam in the less high-energy kV energy range is generated with the aid of the kV X-ray emitter 61. The kV X-ray emitter 61 extends upward toward the kV detector 15. The selected disposition makes it possible for the axis of the kV X-ray beam to coincide spatially with that of an MV X-ray beam emerging from the emitter head 11.

In one embodiment, the MV detector 31 is retracted into the parking position. The kV X-ray emitter 61 and the MV detector 31 are stored in an area where there is not much room. In one embodiment, a mounting and a support do not require a large area and are space saving. In another embodiment, both the mounting and support are retractable into a parking position, so that only the blinds 20 and 21 are visible from the outside of the gantry 10. The mounting and support are hidden behind the blinds 20 and 21. For example, the room available for a patient or a therapist is as large as possible and is free of components that are not required at that time. The respective supports for the kV emitter 61 and the MV detector 31 are embodied such that they can both be extended simultaneously. In this embodiment, for example, the detection of both the high-energy MV X-ray beam and the less high-energy kV X-ray beam is done simultaneously.

In summary of one exemplary embodiment, a support 30 for a radiation therapy system includes a longitudinally adjustable, elongated support arm. The support arm has an arm 32 that is rotatable in the support arm about a first axis perpendicular to the support arm, and a flat detector element. The flat detector element is rotatable in the arm 32 about a second axis that is parallel to the first axis. The detector element is oriented essentially parallel to the support arm. For example, upon rotation of the arm 32, the parallel orientation of the detector element to the support arm is preserved. A motor 40 drives the rotation of the arm 32. The rotation of the arm 32 is driven by a first gear 41 that is connected to the motor 40. The rotation of the detector element is driven by a second gear 45 that is connected to the same motor 40 and operates contrary to the first gear 41. A single motor 40 and two gears 41, 45 operated contrary to one another make very precise positioning possible and at the same time require little structural volume or space.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A medical radiation device support comprising:
   an imaging device with a detector parking space located behind a blind;
   an elongated support arm that is longitudinally adjustable;
   a first arm connected with the support arm, the first arm rotatable about a first axis perpendicular to the support arm;
   a detector connected with the first arm, the detector rotatable about a second axis that is parallel to the first axis, the detector being essentially parallel to the support arm, the detector operative to remain parallel to the support arm during the rotation of the first arm, and
   a motor that is operative to drive the rotation of the first arm,
   wherein a first gear is operative to rotate the first arm and is connected to the motor, and a second gear is operative to rotate the detector and is connected to the motor, the second gear is operative to rotate contrary to the first gear, and
   wherein the support is supported and disposed in the detector parking space.

2. The support as defined by claim 1, wherein the support arm is a telescoping mechanism, having at least one telescoping rail and at least one telescoping arm.

3. The support as defined by claim 2, wherein the motor is connected to the first gear by a shaft.

4. The support as defined by claim 1, wherein the motor is connected to the first gear by a shaft.

5. The support as defined by claim 4, wherein the motor is connected to the second gear by a belt or a chain.

6. The support as defined by claim 5, wherein the arm has a single strut.

7. The support as defined by claim 1, wherein the arm has a single strut.

8. The radiation therapy system as defined by claim 1, wherein the detector is flat.

9. The support as defined by claim 1, wherein the motor is connected to the second gear by a belt or a chain.

10. The support as defined by claim 1, comprising a detector.

11. The support as defined by claim 10, wherein the detector is an X-radiation detector.

12. A radiation therapy system comprising:
    a gantry; and
    a support having a support arm, a first arm that is rotatable about a first axis perpendicular to the support arm, a detector that is rotatable about a second axis that is parallel to the first axis, the detector being essentially parallel to the support arm, and a motor that is operative to drive the rotation of the first arm,
    wherein a first gear is operative to rotate the first arm and a second gear is operative to rotate the detector, the second gear being connected to the motor and operative contrary to the first gear,
    wherein the detector is an X-radiation detector,
    wherein the support arm is supported by the gantry, and
    wherein the gantry includes a detector parking space located behind a blind, and
    wherein the support is supported and disposed in the detector parking space.

13. The radiation therapy system as defined by claim 12, wherein the detector is operative to detect X-radiation having energy on the MV order of magnitude.

14. The radiation therapy system as defined by claim 12, wherein the support comprises:
    only the one support arm with a telescoping rail and a telescoping arm;
    only one single-strut arm supported by the support arm, the single-strut arm being the first arm;
    only one lateral drive mechanism supported by the first arm; and
    only the detector supported by the lateral drive mechanism.

15. The radiation therapy system as defined by claim 12, wherein the support includes the detector.

16. The support as defined by claim 12, wherein the motor is connected to the second gear by a belt or a chain.

17. The support as defined by claim 12, wherein the support arm has a single strut.

18. The support as defined by claim 12, wherein the support arm is a telescoping mechanism, having at least one telescoping rail and at least one telescoping arm.

19. The support as defined by claim 12, wherein the motor is connected to the first gear by a shaft.

* * * * *